US011986253B2

(12) United States Patent
Corpa De La Fuente

(10) Patent No.: US 11,986,253 B2
(45) Date of Patent: May 21, 2024

(54) MOVABLE TRACKER SYSTEM

(71) Applicant: Blue Belt Technologies, Inc., Pittsburgh, PA (US)

(72) Inventor: Cedric Corpa De La Fuente, Pittsburgh, PA (US)

(73) Assignee: Blue Belt Technologies, Inc., Memphis, TN (US)

(*) Notice: Subject to any disclaimer, the term of this patent is extended or adjusted under 35 U.S.C. 154(b) by 1293 days.

(21) Appl. No.: 16/470,903

(22) PCT Filed: Oct. 28, 2016

(86) PCT No.: PCT/US2016/059595
§ 371 (c)(1),
(2) Date: Jun. 18, 2019

(87) PCT Pub. No.: WO2017/075545
PCT Pub. Date: May 4, 2017

(65) Prior Publication Data
US 2020/0085505 A1 Mar. 19, 2020

Related U.S. Application Data

(60) Provisional application No. 62/247,879, filed on Oct. 29, 2015.

(51) Int. Cl.
*A61B 34/00* (2016.01)
*A61B 34/20* (2016.01)
*A61B 90/00* (2016.01)

(52) U.S. Cl.
CPC ...... *A61B 34/20* (2016.02); *A61B 2034/2051* (2016.02); *A61B 2034/2055* (2016.02); *A61B 2034/2065* (2016.02); *A61B 2034/2072* (2016.02); *A61B 2034/2074* (2016.02); *A61B 2090/363* (2016.02); *A61B 2090/3916* (2016.02)

(58) Field of Classification Search
CPC .... A61B 2090/0812; A61B 2090/0811; A61B 2034/2065; A61B 2034/2051
See application file for complete search history.

(56) References Cited

U.S. PATENT DOCUMENTS

| 5,394,457 | A | * | 2/1995 | Leibinger | A61B 90/39 378/162 |
|---|---|---|---|---|---|
| 6,757,582 | B2 | | 6/2004 | Brisson et al. | |
| 8,223,193 | B2 | | 7/2012 | Zhao et al. | |
| 2004/0068263 | A1 | | 4/2004 | Chouinard et al. | |
| 2009/0306499 | A1 | * | 12/2009 | Van Vorhis | A61B 34/20 606/130 |
| 2011/0320153 | A1 | * | 12/2011 | Lightcap | A61B 34/20 702/94 |

(Continued)

OTHER PUBLICATIONS

International Search Report and Written Opinion for PCT/US2016/059595 dated Feb. 2, 2017.

*Primary Examiner* — Rajeev P Siripurapu
(74) *Attorney, Agent, or Firm* — DLA Piper LLP

(57) ABSTRACT

A movable tracking assembly for use with a navigated surgical system has a marked pin and a tracking sleeve that enables detection of axial and rotational movement. The tracking sleeve has a sensor that can detect movement relative to the marked pin and communicate that information to the surgical system. The tracking sleeve also has external trackers for use with an optical tracking camera.

10 Claims, 2 Drawing Sheets

(56) References Cited

U.S. PATENT DOCUMENTS

2014/0148808 A1* 5/2014 Inkpen ................. A61B 90/06
                                              73/866.5
2014/0187949 A1   7/2014 Zhao et al.
2014/0275955 A1* 9/2014 Crawford ............. A61B 5/061
                                              600/409

* cited by examiner

MOVABLE TRACKER SYSTEM

CROSS-REFERENCE TO RELATED APPLICATION

This application is an international application and claims priority to U.S. Provisional Application Ser. No. 62/247,879, filed on Oct. 29, 2015 and entitled "Movable Tracker System".

FIELD OF INVENTION

The present invention relates to the field of surgical tracking devices and more specifically, tracking devices having motion detection and calibration enhancements.

BACKGROUND OF INVENTION

Surgical tracking assistance devices are increasingly used in surgical procedures, such as full or partial joint replacement surgeries, to help track the position of bones and other tissue to reduce the amount of native tissue removed and improve the positioning and fit of implants, for example. One current tracking system creates a reference frame by placing tracking devices on fixed points within the operative field and tracking them via computer. The tracking devices may be reflectors or emitters of RF or EMF signals that are received by a fixed signal detection camera or receiver. The signal detection device may be in a fixed location in the operating room and may receive reflected EMF signals or emitted RF signals.

In order to accurately and precisely track points of interest on a patient during a procedure, the tracking devices must be affixed to rigid body parts of interest, such as the bones on either side of a diseased joint, for example. The tracking system must then be calibrated to create a virtual reference frame whereby the rigid body part locations may be plotted and tracked. Calibration of the tracking system may be performed by a computer, connected to the signal detection device, detecting and in some embodiments triangulating signals from the tracking devices. In order for the calibration and accuracy of the virtual reference frame to be maintained, the trackers must remain rigidly attached to their respective fixed points of interest. It is not uncommon for the calibration of the system to fail during the course of a procedure due to inadvertent movement of a tracker due to incidental contact, for example.

When a tracker is attached to a bone screw, for example, it is possible for it to be bumped and axially rotated. Because the computer system would not know that the tracker had moved relative to the fixed point of interest (the bone screw), the system might register the rotation as movement of the bone, rather than a loss of calibration. As a result, the system's virtual reference frame would no longer accurately correspond to the actual location of the point of interest, and recalibration would be required to regain accuracy. Similarly, any movement introduced to the signal detection device could register as movement of the points of interest and create an inaccurate correspondence between the virtual and actual reference frames.

As a result, there is a need in the surgical motion tracking field to provide the ability for a tracking system to differentiate between incidental movement of a tracker device on a fixed location, and actual movement of the fixed location. The present invention seeks to solve this problem with the introduction of a secondary means of tracking the current standard tracking devices used in tracking assisted surgery.

SUMMARY OF INVENTION

The present invention discloses a tracking assembly that utilizes a positional sensor in conjunction with a pin having a tracking pattern to detect any changes the position of the tracking assembly on a fixed target that they are tracking. A surgical tracking system employing the tracking assemblies of the present invention can detect any incidental movement and displacement in either an axial or a rotational direction using signals from the sensor(s). Data from the sensor(s) will be provided to a tracking data analyzer that can differentiate the movement of the tracking device from movement of the fixed target, such as a bone being tracked. Additionally, because the system can differentiate movement of the tracking assembly from that of the fixed target, the system can also be adapted to allow tracking system elements, such as the camera, to be moved without the need to recalibrate the entire system.

In certain embodiments of the present invention, the positional sensor of each tracking assembly is able to detect movement by sensing a tracking pattern disposed on a marked pin affixed to the fixed target. This tracking pattern may be optical, magnetic, or electromagnetic, which the internal positional sensor can use to determine movement between the fixed target and the tracking sleeve. In certain embodiments, this tracking frame is a gridded index disposed on a pin. This marked pin is slidingly coupled to a tracking sleeve having a generally tube-like shape. In this configuration, the tracking sleeve may be moved in axial and rotational directions that may be detected by the internal positional sensor.

In addition to the various objects and advantages of the present invention which have been described above, various other objects and advantages of the invention will become more readily apparent to those persons skilled in the relevant art from the following more detailed description of the invention, particularly, when such description is taken in conjunction with the attached drawing figures and with the appended claims.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, wherein.

DETAILED DESCRIPTION OF THE INVENTION

The following detailed description includes the best currently contemplated modes of carrying out exemplary embodiments of the invention. The description is not to be taken in a limiting sense, but is made merely for the purpose of illustrating the general principles of the invention.

Figure 1:
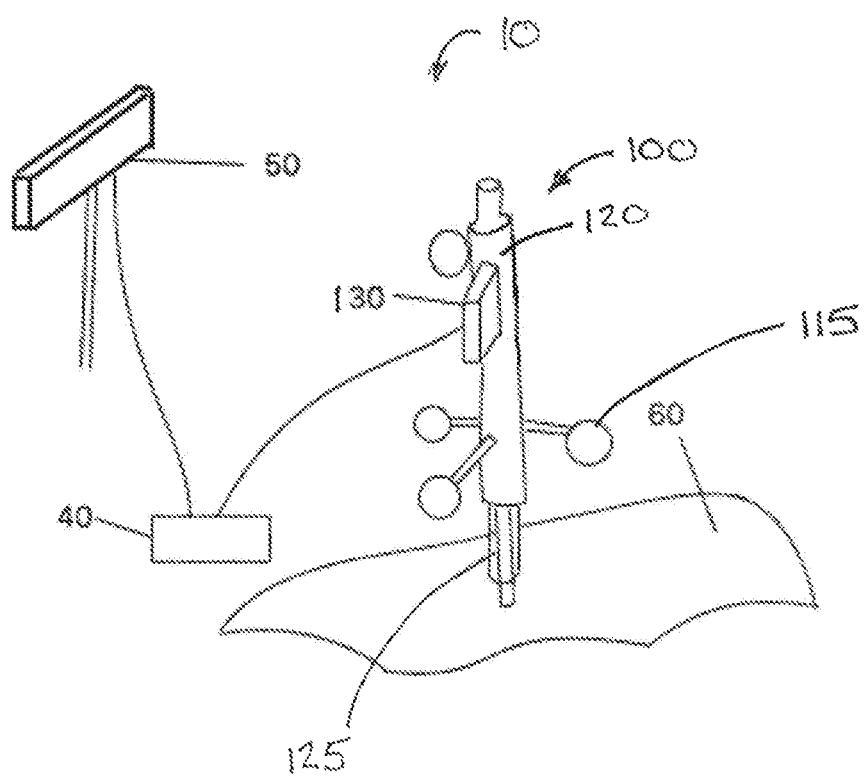
FIG. 1 is a perspective view of a movable surgical tracker assistance system in accordance with an embodiment of the present invention.

FIG. 1 depicts a surgical tracking system 10 constructed in accordance with certain embodiments of the present invention. The system typically includes at least one camera 50 for identifying the locations of one or more trackers within an operative space and which is communicatively connected to a computer system 40 that contains software for interpreting tracker location data from the camera to determine the real-time location of all trackers within a pre-defined reference frame. Patient-specific anatomical information, such as MRI data of the patient's diseased joint or previously collected location points on the bones that make up the joint, has been saved into memory on the computer system 40 so that when the tracker information is combined with the anatomical information, the computer system 40 can be adapted to display the real-time locations of the operative bones in comparison with a surgical plan on a monitor to ensure consistency with the plan. In certain embodiments, a cutting tool is also tracked by the system so that the cutting tool is only operative when it is in a location where the surgical plan requires a cut. A typical system of this type has been disclosed in U.S. Pat. No. 6,757,582 to Brisson et al., the entirety of which is hereby incorporated as if more fully set forth herein.

In certain embodiments, a tracking assembly 100 has a tracking sleeve 120 with external location trackers 115 extending distally from the sleeve 120. In embodiments, the trackers could be optically reflecting, RF emitting, or EMF emitting, depending on the use or the preference of the practitioner. The tracking sleeve 120 is mated to and works with a marked pin 125 that has been implanted into a patient's bone to be tracked. In embodiments, the marked pin 125 may be a bone screw, a probe, or any other implement that can be rigidly affixed to a portion of a patient to be tracked. Likewise, the tracking sleeve 120 may be a cannula that can be coupled with a surgical instrument to determine its position. In certain embodiments, the marked pin 125 is fixably attached to a rigid body part, such as a bone, that is being tracked and serves as a fixed point of reference for the body part in all reference frames.

The position and orientation of the tracking assembly 100 is determined by the computer system 40 which constantly monitors the surgical tracking system 10, determines if there is any change in position of any tracking devices relative to the bones they are being used to track and correspondingly determines the new position of the tracking devices in a virtual reference frame. The computer system 40 may be computer hardware and software designed to work with the surgical tracking system 10 or it may be electronic components and software that are not part of the surgical tracking system 10. When the tracking system 10 is first initialized, the computer system 40 calibrates a virtual reference frame to correspond to the actual location of the tracking devices and corresponding points of interest, such as bones to be prepared. The tracking system 10 also creates the virtual reference frame by determining the relationship between each tracking assembly 100 and the surgical tracking system 10. Calibration may also require certain initial positioning of the points of interest, such as positioning the fixed points of interest in a "start" position, that may be required for certain surgical procedures.

In certain embodiments, the tracking sleeve 120 contains an internal positional sensor 130 that tracks the position of the tracking sleeve 120 in relation to the marked pin 125 such that it is able to detect axial and rotational movement of the tracking sleeve 120 relative to the marked pin 125 and is configured to send any such relative motion data to the tracking computer system 40 via a data bus (not shown) either wirelessly or via wires. The internal positional sensor 130 may use optical, magnetic or electromagnetic sensing technologies to detect axial and rotational movement of the tracking sleeve 120 relative to the marked pin 125. In certain embodiments, the internal positional sensor 130 is a reflective encoder that combines an emitter and a detector for detecting location relative to a codewheel or linear codestrip, such as may be placed on the marked pin 125. Alternatively, the pin could be laser etched for an optical sensor or a groove or chemical deposit could be used if the tracking sleeve 120 contains an inductive sensor. In this way, internal positional sensor 130 translates rotary and/or axial motion into digital outputs. The internal positional sensor 130 may preferably be in digital communication with the tracking computer system 40 via a wired or wireless data connection in order to pass on the digital outputs indicative of relative movement, such as from an inadvertent bump by a member of a surgical team The computer system 40 must perform several reference frame transformations in order to determine the absolute position of the marked pin 125 and thus the body part being tracked. These reference frame transformations are performed using the tracking data and digital outputs collected by the internal positional sensor 130 and tracking system 10. The computer system 40 is then able to calculate and plot the accurate position of the marked pin 125 as it corresponds to the virtual reference frame. All of this information can then be displayed on a monitor for the surgeon and employed with a smart tool to avoid unwanted cuts.

In certain embodiments, the initialization process includes an initial registration of the marked pin 125 within the tracking system reference frame, which allows for the computer system 40 to translate movements of the tracking sleeve 120 relative to the marked pin 125. Translating any movements of the tracking sleeve 120 relative to the marked pin 125 enables the computing system 40 to compensate in real-time for any unintentional movement of the tracking sleeve 120 relative to the patient 60.

Figure 2:
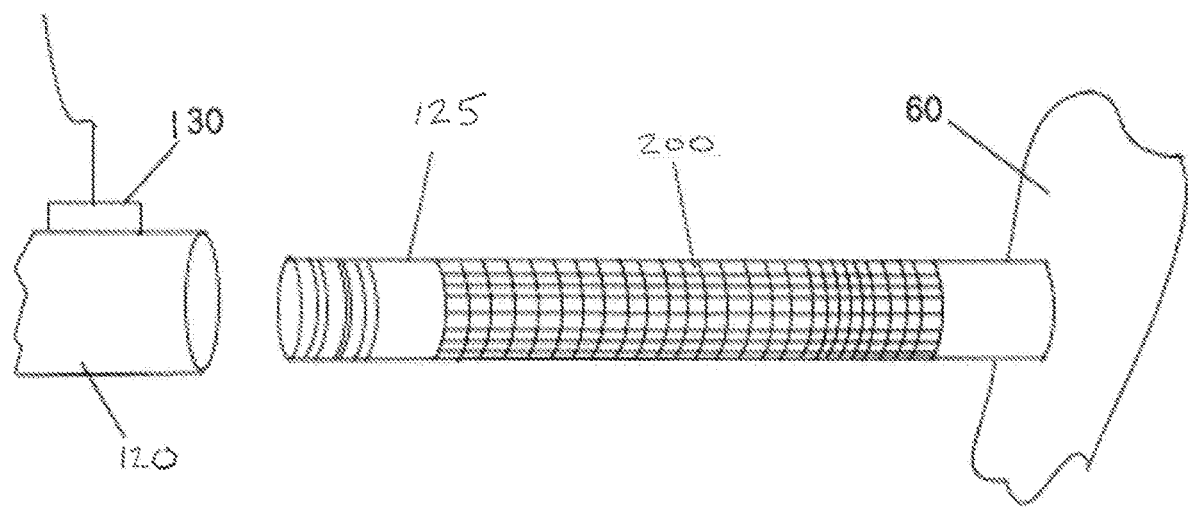
FIG. 2 is an exploded view of a modified surgical tracker constructed in accordance with a preferred embodiment.

FIG. 2 provides an exploded close-up illustration of an embodiment of the tracking assembly 100, which includes the tracking sleeve 120 and marked pin 125 with a tracking pattern 200 in accordance with certain embodiments of the invention. The tracking sleeve 120 comprises a generally hollow tube that slidingly couples with the marked pin 125. Once slidingly coupled, as demonstrated in FIG. 1, tracking sleeve 120 may move axially as well as rotate about the axis of the marked pin 125. The tracking pattern 200 appears uniform in FIG. 2, but in certain embodiments, the tracking pattern 200 may include localized variations, such as denser grid lines, to enable more precise positional tracking of the tracking sleeve 120 in relation to the marked pin 125.

Internal positional sensor 130 is disposed on the tracking sleeve 120 to monitor the position of the tracking sleeve 120 in relation to the tracking pattern 200 that has been encoded on the marked pin 125. In certain embodiments, the tracking pattern 200 is an optical index pattern that the internal positional sensor 130 can detect. When the tracking sleeve 120 is initially placed on the marked pin 125, the internal positional sensor 130 detects its location on the tracking pattern 200 and transmits that data to the computer system 40. In certain embodiments, the optical index pattern forms a grid that comprises latitudinal and longitudinal marks about the marked pin 125. The tracking pattern 200 is rigidly affixed, imprinted on, or otherwise immovably emblazoned on the marked pin 125 such that any movement of the tracking sleeve 120 in relation to the marked pin 125 can be taken into account with calculating the exact position and location of the patient's relevant body parts. The precision of the tracker assembly 100 can vary depending on how finely the pattern is etched or marked on the pin 125.

In certain embodiments, when first installing the tracking sleeve 120 by sliding it onto the marked pin 125, the internal positional sensor 130 reads the marks on the tracking pattern 200 to determine the initial pattern location after the tracking sleeve 120 is placed. These initial conditions may then be stored by the computer system 40. Thereafter, by continuously monitoring any change in location on the marked pattern 200, the internal positional sensor 130 can be used to determine the relative axial and rotational displacement of the tracking sleeve 120 as it is moved up and down or rotated about the marked pin 125. The tracking computer system 40 can then use the data from the internal positional sensor 130 to interpret and differentiate rotational and axial displacement of the tracking sleeve 120 from actual movement of the marked pin 125 and the corresponding body part being tracked. In some embodiments, the tracking pattern 200 can use 2D bar code or quick-read (QR) code type technology to form a unique two-dimensional pattern on the marked pin 125, which can be read by internal positional sensor 130 to allow computer system 40 to decode unique relative positions between the tracking sleeve 120 and the marked pin 125. In other embodiments, an indicia could be disposed on the marked pin 125 to be read by the internal positional sensor 130 whereby the indicia identifies the size, pattern, dimensions, or other unique features of the tracking pattern 200 to enable the computer system 40 to interpret digital outputs received from the internal positional sensor 130 and display the precise position of the tracker assembly 100 in relation to the surgical field.

In certain embodiments, magnetic or electromagnetic indices may be used to create the tracking pattern 200 on the marked pin 125. For the internal positional sensor 130, technology such as an IC-OG optical encoder sensor may be used (e.g., a 8-bit differential scanning opto encoder). Similarly, known magnetic and electromagnetic encoders may be utilized for the internal positional sensor 130 with corresponding magnetic or electromagnetic tracking patterns 200.

An additional benefit to the modified tracking system of the present invention is that the surgical tracking system 10, or individual tracking assemblies 100, may be moved mid-procedure without the need to recalibrate the entire system. Since the modified tracking system allows for the monitoring of the orientation of the tracking sleeve 120 as it is coupled to the marked pin 125, the computer system 40 can differentiate real-time changes in placement of the tracking camera 50 from changes of orientation or movement of the tracking sleeve 120 in relation to the marked pin 125. As a result, accidental or intentional movement of the camera 50 will not result in inaccuracies being introduced into the virtual reference frame or for the need to recalibrate.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain and which fall within the limits of the appended claims.

I claim:

1. A navigated surgical system comprising:
   a camera;
   a computer system in data communication with the camera; and
   at least one tracking assembly comprising a tracking sleeve and a marked pin having an optical grid-based tracking pattern varying in both a longitudinal direction and a latitudinal direction,
   wherein the tracking sleeve has external location trackers that can be detected by the camera and an internal position sensor in data communication with the computer system,
   wherein the tracking pattern comprises variations in grid line density, in at least one of the longitudinal direction and the latitudinal direction, to enable varying precision of positional tracking at different localities, and
   whereby the computer system is configured to determine the location of the tracking assembly through detection the external location trackers within a reference frame and to correct for any movement of the tracking sleeve in relation to the marked pin.

2. The navigated surgical system of claim 1, wherein the marked pin has a first portion structured for implantation into an object to be tracked and a second portion having the tracking pattern disposed thereon, the pattern detectable by the internal positional sensor for determining movement of the tracking sleeve in relation to the marked pin and communicating that movement to the computer system.

3. A method of reducing error in a navigated surgical system, the method comprising:
   affixing at least one marked pin to a bone to be tracked, the marked pin having an optical grid-based tracking pattern varying in both a longitudinal direction and a latitudinal direction;
   disposing a tracking sleeve onto each marked pin, the tracking sleeve including an internal tracking sensor and a plurality of external location trackers;
   detecting position information from the internal tracking sensor by detecting grid lines of varying density, in at least one of the longitudinal direction and the latitudinal direction;
   detecting a position of the tracking sleeve from the plurality of external location trackers; and
   determining, based on the position information, whether any relative movement between the position of the tracking sleeve and the bone has occurred.

4. The method of claim 3, further comprising:
   compensating for the relative movement between the position of the tracking sleeve and a tracking target in response to determining that relative movement has occurred; and
   displaying corrected location data.

5. The navigated surgical system of claim 1, wherein the external location trackers comprise one or more of optically reflecting trackers, RF emitting trackers, and EMF emitting trackers.

6. The navigated surgical system of claim 1, wherein the internal tracking sensor further comprises a data bus communicatively connected with the navigated surgical system for transferring movement information.

7. The navigated surgical system of claim 1, wherein the internal tracking sensor comprises one or more of a reflective encoder and an optical sensor.

8. The navigated surgical system of claim 1, wherein the marked pin is configured to be fixably attached to a patient's bone.

9. The navigated surgical system of claim 8, wherein the marked pin has a first end that is threaded.

10. The navigated surgical system of claim 1, wherein the marked pin comprises indicia for identifying the tracking pattern.

\* \* \* \* \*